United States Patent
Lou et al.

[11] Patent Number: 5,729,042
[45] Date of Patent: Mar. 17, 1998

[54] RAISED FUSE STRUCTURE FOR LASER REPAIR

[75] Inventors: Yung-Song Lou, Ruey-Tung; Ching-Cherng Rou, Shan-Wang Shiang; Ting Chou, Ne-Hu; Chao-Ming Koh, Pao-Shan; Shin-Chi Lee, Chu-Tung; Chuen-Nan Chen, Hsin chu, all of Taiwan

[73] Assignee: Vanguard International Semiconductor Corporation, Hsinchu, Taiwan

[21] Appl. No.: 831,877

[22] Filed: Apr. 2, 1997

Related U.S. Application Data

[63] Continuation of Ser. No. 514,800, Aug. 14, 1995, abandoned.

[51] Int. Cl.$^6$ .................................................. H01L 29/00
[52] U.S. Cl. ...................... 257/529; 428/601; 428/700; 428/958
[58] Field of Search ..................... 257/529; 438/132, 438/601, 700, 958

[56] References Cited

U.S. PATENT DOCUMENTS

| | | | |
|---|---|---|---|
| 4,455,194 | 6/1984 | Yabu et al. | 257/529 |
| 4,536,949 | 8/1985 | Takayama et al. | 29/578 |
| 4,598,462 | 7/1986 | Chandrasekhar | 257/529 |
| 4,748,491 | 5/1988 | Takagi | 257/529 |
| 4,853,758 | 8/1989 | Fischer | 257/529 |
| 4,908,692 | 3/1990 | Kikuchi et al. | 257/529 |
| 5,025,300 | 6/1991 | Billig et al. | 357/51 |
| 5,241,212 | 8/1993 | Motonami et al. | 257/529 |
| 5,444,012 | 8/1995 | Yoshizumi et al. | 257/529 |
| 5,538,924 | 7/1996 | Chen | 257/529 |

*Primary Examiner*—J. Carroll
*Attorney, Agent, or Firm*—George O. Saile; Stephen B. Ackerman

[57] ABSTRACT

A novel raised polycide fusible link structure is described. This structure enables a highly reliable laser-cutting process to be used in which the fuse can be easily and totally severed over a wide range of laser energy levels. The primary feature of the structure is that the fusible link is located on a pedestal that raises it above the surface of the main body of the integrated circuit, thereby providing a measure of thermal isolation for the fuse when it is irradiated by the laser. An efficient process for manufacturing the structure is also described.

6 Claims, 2 Drawing Sheets

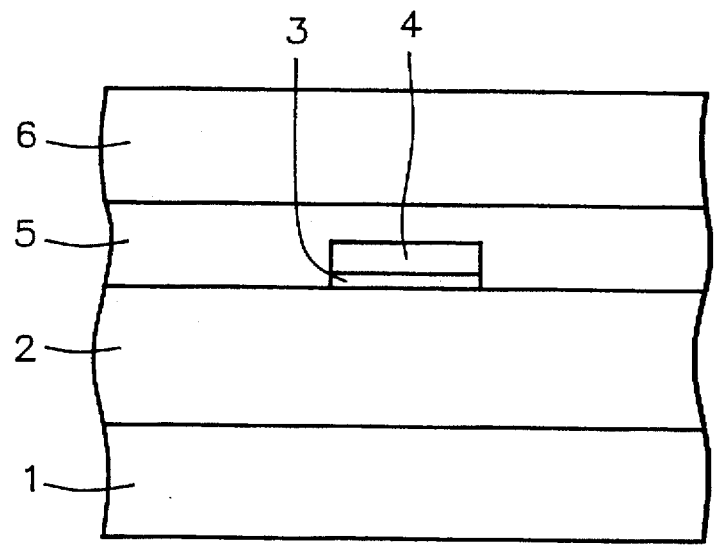
*FIG. 1 - Prior Art*
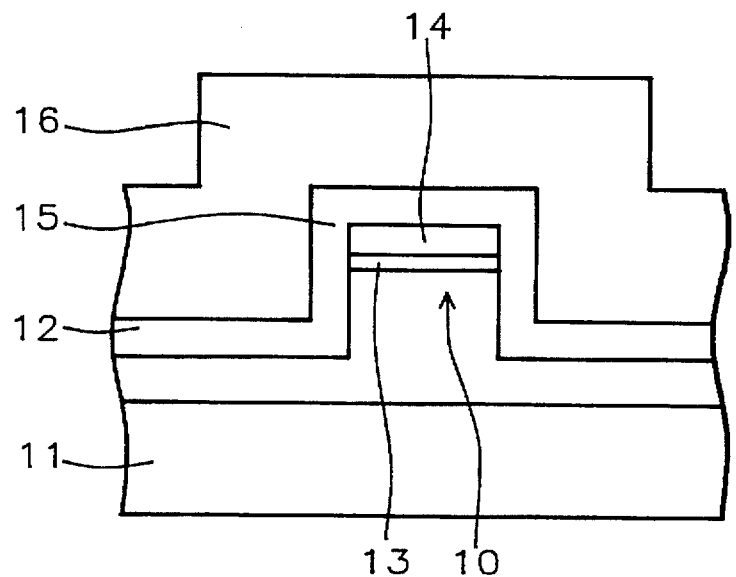
*FIG. 2*

RAISED FUSE STRUCTURE FOR LASER REPAIR

This is a continuation of Ser. No. 08/514,800, filed on Aug. 14, 1995, abandoned.

BACKGROUND OF THE INVENTION

(1) Field of the Invention

The invention relates to the general field of semiconductor integrated circuits, more particularly to circuits that may be personalized, repaired or modified by means of fusible links.

(2) Description of the Prior Art

Semiconductor integrated circuits (ICs) that have optimum density and/or performance cannot, in general, be repaired or modified. There exists, however, a large class of ICs that are intended to be repairable and/or modifiable. In certain cases, no real circuit exists until the IC has been personalized by breaking certain connections, thereby determining how the components are to be connected to one another.

One method for realizing circuits of this type is to arrange for some of the connections between components to be capable of being permanently removed (opened) as desired. The portion of such a connection that is actually physically removed is referred to as a fusible link.

In general, the method for removing a particular fusible link comprises heating it briefly, but with sufficient intensity so that it vaporizes without appreciably heating other circuitry in its vicinity. Delivery of the heat pulse that is required to produce the selective vaporization of any particular fusible link is achieved in one of two ways. An X-Y addressing scheme may be used to deliver a high current pulse to the link so that vaporization occurs as a result of Joule heating or a high energy beam of intense laser light may be directed at the surface of the fusible link for a short time.

A common problem, associated with both methods of vaporizing fusible links, is that some, or all, of the debris that is a byproduct of said vaporization process recondenses on the surface of the IC and may cause short circuiting. This is commonly dealt with by coating the entire integrated circuit with a layer of insulation as a final step in the manufacturing process, thereby electrically isolating it from any conductive material that may recondense on it. Said final layer of insulation also covers the fusible links, thereby increasing the mass of material that must be vaporized whenever a particular link is to be blown.

Ideally, all the heat energy that is directed at a particular fusible link will be used for effecting its vaporization. In practice, some of this energy will be conducted into the substrate, or main body of the integrated circuit, away from the fusible link. Thus it will not be available for the vaporization process and, additionally, it may have an undesirable effect on the integrated circuit itself. This phenomenon can lead to a narrowing of the process window that is available for heating the link—too little energy and vaporization of the link is incomplete, too much energy and surrounding circuitry gets damaged.

A number of issued patents address various aspects of these two problems. Takagama (U.S. Pat. No. 4,536,949 August 1985) is concerned with electrical (as opposed to laser) fusing. The fusible link sits at the bottom of a deep trench on whose walls the products of vaporization are expected to condense, thereby keeping them away from other parts of the integrated circuit. Billig et al. (U.S. Pat. No. 5,025,300 June 1991) is concerned with laser fused links and is similar to Takagama in that the link lies at the bottom of a trench. Unlike Takagama, Billig also makes use of a final protective layer of insulation.

Monotami et al. (U.S. Pat. No. 5,241,212 August 1993) also place the fuse in a trench but the protective layer stops at the trench's top edge, thereby leaving the link itself exposed. The upper surface of the fusible link is level with the bottom of the trench. In an alternative, optional, embodiment, a layer of insulation 6–8,000 Angstrom units thick is deposited over the fuse. The fuse is heated through laser energy, most of which passes through this optional layer.

An example of a fusible link structure of the type found in the prior art is shown in FIG. 1 as a schematic cross-section. The fusible link (layers 3 and 4) lies on silicon dioxide layer 2 which has been formed on the surface of silicon substrate 1 which comprises the integrated circuit. The fusible link has been overcoated with passivation layers 5 and 6.

Experiments on fusible link structures such as the one illustrated in FIG. 1 have shown that the range over which the applied laser energy may vary is quite narrow. For example, as shown in FIG. 3, over an energy range of from 0 to 2 microjoules, the minimum energy required to cause links to open up was found to be about 0.5 microjoules. However, between 0.5 and 1 microjoule, the resistance of links that had been subjected to laser pulses was found to vary over a wide range, from short to open circuits. Between 1 and 1.5 microjoules, links that had been subjected to laser pulses were consistently found to have open circuited, as intended. However, in the range of from 1.5 to 2 microjoules, a wide variation in link resistance, similar to what was seen for the 0.5 to 1 microjoule range, was again seen. In the latter case, the cause was identified as being the result of heat reaching the underlying silcon substrate in amounts suficient to melt some of the silicon, which then contributed to the recondensed debris.

It should also be noted that, for laser heated links in general, the duration of the laser pulse will always be slightly longer than the minimum time needed to cause the link to explode. This is inevitable, given that the exact energy needed varies slightly from link to link. As a consequence, the underlying material on which the link rested prior to its explosion will be directly exposed to the laser for a short time.

SUMMARY OF THE INVENTION

It is an object of the present invention to provide a fusible link structure, opened via laser irradiation, said opening process to have no side effects, such as occasional short circuiting.

A further object of the present invention is to provide a fusible link that may be opened by means of laser irradiation over a wide range of laser energies.

Yet another object of the present invention is to provide a process for manufacturing a fusible link having these characteristics, said process to cost little or nothing more than the processes used to manufacture other types of fusible link.

These objects have been achieved in a structure in which the fusible link is located on a pedestal that raises it above the surface of the main body of the integrated circuit, thereby providing a measure of thermal isolation for the fuse when it is irradiated by the laser. A process for manufacturing this structure is described in which the link acts as its own self-aligned mask during the formation of said pedestal.

BRIEF DESCRIPTION OF THE DRAWINGS

FIG. 1 is a schematic cross-section of a fusible link structure based on prior art.

FIG. 2 is a schematic cross-section of a fusible link structure based on the present invention.

DESCRIPTION OF THE PREFERRED EMBODIMENTS

Figure 3:
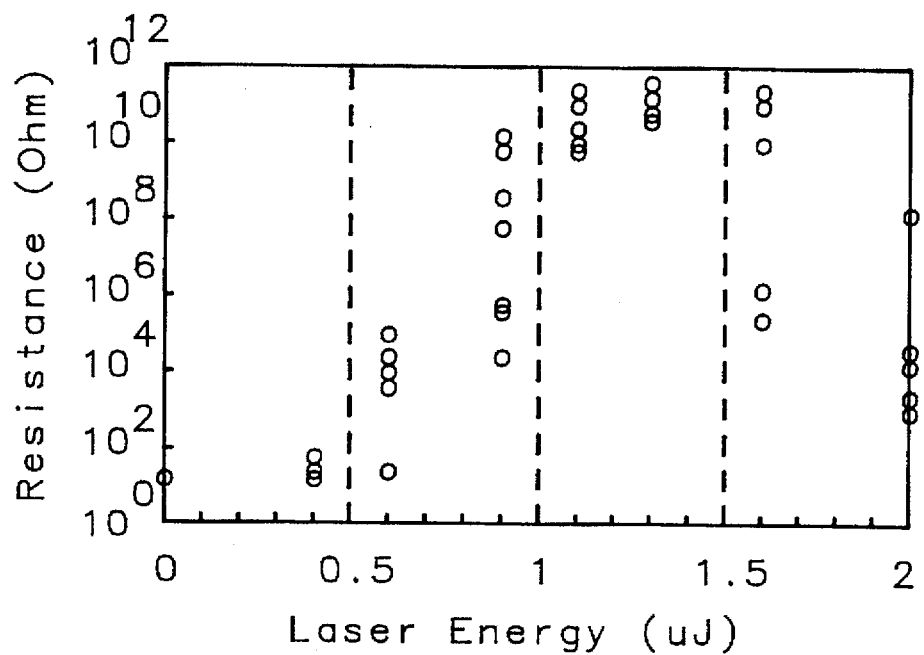
FIGS. 3 and 4 show the results of laser irradiation of the designs of FIGS. 1 and 2 respectively, over a range of incident laser energies.

We will now describe a typical embodiment of the present invention which overcomes the deficiencies in the prior art that were described above. Referring to FIG. 2, we show, in schematic cross-section, a pedestal 10, of silicon oxide, resting on layer 12 of the same material. Layer 12 lies on the surface of silicon substrate 11, which comprises the integrated circuit. While silicon oxide is the preferred material for pedestal 10, the invention will still operate successfully with any similar material that has relatively low thermal conductivity. For successful operation, the thickness of the pedestal may range from about 1,000 to 9,000 Angstrom units, about 5,000 Angstrom units being preferred. The thickness of insulating layer 12 immediately beneath the pedestal is typically about 4,000 Angstrom units, but any thickness in the range of about 1,000 to 10,000 Angstrom units would be satisfactory.

The fusible link itself comprises two layers. Layer 13 comprises polycrystalline silicon, heavily doped to increase its conductivity. Typically, the dopant used was phosphorus at an implanted dose of about $5 \times 10^{15}$ atoms/sq. cm. Although layer 13 could have a thickness in the general range of from 100 to 2,000 Angstrom units, we have typically used a value of about 500 Angstrom units. Layer 14 comprises tungsten silicide, deposited through chemical vapor deposition, typically about 1,500 Angstrom units thick, although any thickness in the range of about 500 to 3,000 Angstrom units would be satisfactory.

In order to manufacture the structure of FIG. 2, layers 2, 3, and 4 (as shown in FIG. 1) were first deposited onto the surface of the integrated circuit. Thereafter, the fusible link (comprising layers 3 and 4 in FIG. 1) was patterned, using conventional photolithographic techniques, into appropriate shapes that served to connect various parts of the integrated circuit that might, or might not, be severed at a later time, as needed. The patterned fuse links were now used as self-aligned masks while about 5,000 Angstrom units of layer 2 were etched away. This was followed by the deposition of passivating layers 15 and 16, giving the finished structure the appearance shown in FIG. 2.

Note that (in FIG. 2) layer 15 comprises about 2,000 Angstrom units of boro-phosphosilicate glass, although any thickness in the range from 0 to about 7,000 Angstrom units would work, while layer 16 comprises about 6,500 Angstrom units of silicon nitride (deposited by means of Plasma Enhanced Chemical Vapor Deposition) although any thickness in the range from 0 to about 7,000 Angstrom units would still work.

In order to evaluate the invention and, particularly, to compare it to the prior art, a structure embodying the present invention (as illustrated in FIG. 2) was compared with a structure of the type illustrated in FIG. 1. The thicknesses of the various layers involved was the same in both cases, the principal difference being the pedestal geometry of the present invention versus the planar geometry of the prior art example.

The laser used for effecting the explosion of the fusible links was a 1047 nm Q-switched Nd-doped Yttrium Lanthanum Fluoride (YLF) laser. The laser energy was normally in the range between 0.8 and 1.2 microjoules with a spot diameter of 5 microns and a pulse width of 35 ns. To determine whether or not a given link had been successfully blown, an electrical continuity measurement was performed by applying a constant voltage across the blown fuse and then measuring the passing current. The fuse was considered to have been blown successfully (be in an open state) if the measured resistance was greater than 10 megohms.

Figure 4:
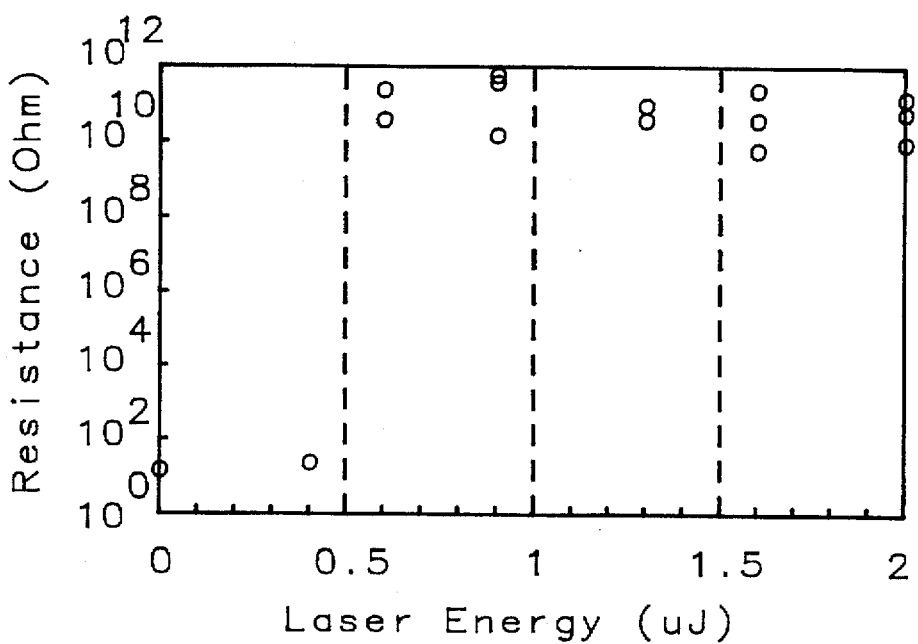

The results of the above described experiments are illustrated in FIGS. 3 and 4. FIG. 3 is for the planar (prior art) structure. Four distinct regions are shown in the figure, each reflecting different explosion characteristics of the links. In the region of 0 to 0.5 microjoules, the resistance measurements always showed a shorted state, indicating that the incident laser energy was below the threshold level needed to evaporate the fusible link (and the passivating layers above it).

In the region of 0.5 to 1.0 microjoules, a wide range of resistance values was observed. In this energy range the laser heating produced a liquid pressure high enough to fracture the passivating layers. However, due to strong optical absorption by both the silicide layer and the passivating layers, some of the ejected link material may be redeposited around the crater and lead to full or partial short circuiting.

In the region of 1.0 to 1.5 microjoules, the process worked as intended and an electrically open state was obtained for all cases. This implies that the applied energy was sufficient to fully vaporize the link and direct the debris away from the crater.

In the region of 1.5 to 2.0 microjoules, the resistance was again found to vary over a substantial range, similar to that observed for the 0.5 to 1.0 microjoules region. Cross-sectional micrographs showed that this was due to laser energy having caused the underlying silicon substrate to become heated to a sufficient degree for some of it to be evaporated and contribute to the debris.

The above results illustrate that, with the planar design of the prior art, the process window for laser energy application is rather narrow. In contrast, consider the results illustrated in FIG. 4 which are for a fusible link structure based on the present invention. As can be seen, once the threshold energy of 0.5 microjoules has been exceeded, all links, after laser induced explosion, were found to be fully open circuited, independent of the laser energy, to at least 2 microjoules. These results confirm that the pedestal design of the present invention serves to confine the laser induced heat to the immediate vicinity of the fusible link, thereby greatly minimizing the side-effects associated with the planar design.

While the invention has been particularly shown and described with reference to this preferred embodiment, it will be understood by those skilled in the art that various changes in form and details may be made without departing from the spirit and scope of the invention.

What is claimed is:

1. A method for manufacturing a fusible link structure comprising:

providing a silicon integrated circuit;

depositing a first insulating layer;

depositing a fusible link layer;

patterning said fusible link layer into a shape that is suitable for it to be part of the integrated circuit;

using said patterned fusible link layer as a mask, removing between 4,000 and 9,000 Angstroms of said first insulating layer, thereby forming a pedestal on which said patterned fusible link layer lies; and then coating the structure with a second insulating layer.

2. The method of claim 1 wherein said first insulating layer comprises silicon oxide.

3. The method of claim 1 wherein the step of coating the structure with said second insulating layer further comprises depositing a layer of boro-phosphosilicate glass and then depositing a layer of silicon nitride.

4. The method of claim 1 wherein said second insulating layer is deposited to a thickness that is between 0 and about 14,000 Angstrom units.

5. The method of claim 1 wherein the step of depositing a fusible link layer further comprises depositing a layer of polycrystalline silicon and then depositing a layer of tungsten silicide.

6. The method of claim 1 wherein the fusible link is deposited to a thickness that is between about 5,00 and about 5,000 Angstrom units.

* * * * *